(12) United States Patent
Doerr

(10) Patent No.: US 8,073,542 B2
(45) Date of Patent: Dec. 6, 2011

(54) METHOD FOR SECURE REPROGRAMMING OF CLINICALLY RELEVANT PARAMETERS AS PART OF REMOTE PROGRAMMING OF AN ELECTRONIC IMPLANT

(75) Inventor: Thomas Doerr, Berlin (DE)

(73) Assignee: BIOTRONIK CRM Patent AG (CH)

( * ) Notice: Subject to any disclaimer, the term of this patent is extended or adjusted under 35 U.S.C. 154(b) by 841 days.

(21) Appl. No.: 12/134,519

(22) Filed: Jun. 6, 2008

(65) Prior Publication Data

US 2009/0043360 A1 Feb. 12, 2009

(30) Foreign Application Priority Data

Aug. 11, 2007 (DE) .......................... 10 2007 037 948

(51) Int. Cl.
*A61N 1/08* (2006.01)
(52) U.S. Cl. ................. 607/30; 607/31; 607/32; 607/60
(58) Field of Classification Search .................... 607/30, 607/31, 32, 60
See application file for complete search history.

(56) References Cited

U.S. PATENT DOCUMENTS

| | | | |
|---|---|---|---|
| 4,253,466 A | 3/1981 | Hartlaub | |
| 6,535,766 B1 | 3/2003 | Thompson et al. | |
| 7,460,912 B2 | 12/2008 | Hoyme et al. | |
| 2003/0114897 A1 * | 6/2003 | Von Arx et al. ................. | 607/60 |
| 2005/0245992 A1 | 11/2005 | Persen et al. | |
| 2005/0251227 A1 | 11/2005 | Khoo et al. | |
| 2006/0161222 A1 | 7/2006 | Haubrich | |
| 2009/0076570 A1 | 3/2009 | Hoyme et al. | |

FOREIGN PATENT DOCUMENTS

| | | |
|---|---|---|
| DE | 100 53 116 A1 | 5/2001 |
| EP | 10 48 323 A2 | 11/2000 |
| WO | WO 2006/055131 | 5/2006 |
| WO | WO 2006/130060 A1 | 12/2006 |

* cited by examiner

*Primary Examiner* — Scott Getzow
*Assistant Examiner* — Joseph Dietrich
(74) *Attorney, Agent, or Firm* — Craig A. Fieschko, Esq.; DeWitt Ross & Stevens S.C.

(57) ABSTRACT

The invention relates to a remotely programmable personal medical device, in particular a programmable implantable medical device, e.g., a cardiac pacemaker, a defibrillator, a cardioverter or the like. In addition, the invention relates to an arrangement for remote programming of such a personal medical device and a method for remote programming of a programmable personal medical device.

20 Claims, 5 Drawing Sheets

METHOD FOR SECURE REPROGRAMMING OF CLINICALLY RELEVANT PARAMETERS AS PART OF REMOTE PROGRAMMING OF AN ELECTRONIC IMPLANT

FIELD OF THE INVENTION

The invention relates to a remotely programmable personal medical device, in particular a programmable implantable medical device, e.g., a cardiac pacemaker, a defibrillator, a cardioverter or the like. Furthermore, the invention relates to an arrangement for remote programming of such a personal medical device and a method for remote programming of a programmable personal medical device.

BACKGROUND OF THE INVENTION

Medical, physiological or operational data obtained by a cardiac pacemaker or defibrillator may be transferred to a central service center for this data to be analyzed at the service center and made available to an attending physician via an appropriate user interface.

Some functions of such implants are controlled by software or firmware and are therefore programmable. The implants therefore have a programmable controller for controlling these functions.

It often happens that after initial programming shortly before, during or after implantation of the implant, additional programming or reprogramming is desirable to be able to better adjust the implant to possible changes in the health of a patient occurring in the meantime or to otherwise improve the performance of the implant. Such programming or reprogramming often occurs via a short-range wireless data to a particular implant link established by the physician with the help of a programming device, with the physician programming the implant in the presence of the patient.

However, programming or reprogramming of an implant may instead be done from a remote location, e.g., via the central service center. To this end, a data link may be established between the service center and a patient intermediary device. The patient intermediary device is usually in the vicinity of the patient and serves more or less as a relay station between the implant and the service center. Therefore, the patient intermediary device has two different bidirectional data communication interfaces to allow a bidirectional data communication with the implant at one end and a bidirectional data communication with the service center at the other end. The data communication interface for the connection between the patient intermediary device and the service center may be designed for wireless or wired connection, e.g., via a cellular phone network or via a landline telephone network.

Whereas traditional programming of an implant is performed with the help of a programming device by a physician in the presence of the patient, the physician does not see the patient in remote programming. The physician does not have the patient directly in front of him when performing the remote programming and therefore cannot respond as easily to direct statements/communications by the patient.

SUMMARY OF THE INVENTION

The inventors have discovered that this circumstance should be taken into account in designing the implant and in arranging for remote programming of the implant.

According to this invention, a programmable personal medical device of the type discussed has two data communication interfaces for a wireless data transmission of data to and from the programmable personal medical device. Programming commands can be sent via both data communication interfaces to the personal medical device. Programming instructions are data packets containing values for control parameters that determine the functioning of a programmable controller of the personal medical device and thus determine the operational performance of the personal medical device itself.

The first data communication interface serves the purpose of local programming of the personal medical device from the immediate vicinity, e.g., using a traditional programming device. If the personal medical device is an implant, the programming of the personal medical device is performed via the first data communication interface in the presence of the patient.

The second data communication interface serves the function of remote programming of the personal medical device. The first and second data communication interfaces differ, e.g., with regard to the transmission technique required for the data transmission, e.g., modulation or corresponding electromagnetic signals or through the data format.

A programmable controller of the programmable device as mentioned above is designed for implementing the control of functions of the personal medical device on the basis of control parameters. The control parameters may assume different parameter values, which lead to different functions. For example, with a cardiac pacemaker the strength of a ventricular stimulation pulse—expressed in volts or milliamperes—is a control parameter that may assume various parameter values. A suitable parameter value for the strength of a ventricular stimulation pulse is usually determined by stimulus threshold tests by the physician or the device itself. Other parameter values are preselected for the personal medical device by programming without prior testing. To allow such programming, the programmable controller is connected to the first and/or the second data communication interfaces and can receive the parameter values for the control parameters of the personal medical device via these programming instructions.

To be able to store such parameter values, the personal medical device has a memory connected to the programmable controller.

According to the invention, the programmable controller and the memory are designed in connection to one another, so that in addition to an instantaneous parameter value, at least a categorical characterization can be stored for at least some of the control parameters of the externally programmable personal medical device. The categorical characterization identifies the corresponding control parameter as belonging to at least one of at least two categories. The first category of control parameters have parameter values which are not initially set as a test for a short period of time before then being confirmed for permanent use, but which instead are set from the beginning without having to wait for a response by the patient to the change in the control parameters. The second category relates to control parameters that are not to be programmed immediately with permanent values, but which instead are first tested for a short period of time to be able to test the effect of reprogramming before these control parameters are then either reset or reprogrammed permanently.

For a personal medical device such as a cardiac pacemaker or defibrillator, the first category includes control parameters which can be reprogrammed in follow-up care with direct patient contact if needed, but where monitoring of the new parameter settings during follow-up care is not possible or customary. The second category of control parameters includes control parameters that must be checked by the physician with regard to patient safety as part of follow-up care after reprogramming, or that must first be checked by means of a temporary program.

The respective control parameters of assigned stored categorical characterizations determine the behavior of the programmable controller after receiving a programming instruction via the second data communication interface, so that (1) after execution of a programming instruction containing only allowed parameter values for control parameters of a first category, these parameters are stored permanently in the memory as instantaneous parameter values, so that the function of the programmable controller is henceforth determined by these parameter values until receipt of another programming instruction; and (2) after execution of a programming instruction which contains only allowed parameter values for control parameters of the second category, these parameter values are stored in the memory as instantaneous parameter values for a predetermined limited period of time, so that the function of the programmable controller and thus the function of the personal medical device is determined by these parameters until the end of this predetermined period of time and then is determined again by the parameter values originally set.

The personal medical device is preferably designed through appropriate cooperation of programmable controllers and memories to allow receipt of programming instructions containing allowed parameters for control parameters of both a first and a second category.

In one version of the invention, the programmable controller is designed so that all parameters are stored as instantaneous parameters in the memory for a predetermined limited period of time, so that the function of the programmable controller is determined by these parameter values until the end of the predetermined period of time and then again by the parameter values set previously. This means that even the control parameters provided from the beginning for permanent reprogramming are initially reprogrammed only temporarily when they are reprogrammed together with control parameters of the second category. This ensures that all control parameters that are reprogrammed at the same time are consistent with one another because it is possible for the concrete choice of the first control parameters to be coordinated with the second control parameters that are reprogrammed at the same time.

Alternatively, the programmable controller could be designed so that after receipt of a programming instruction containing parameter values for control parameters of both the first category and the second category, the parameter values of the control parameters of the first category are stored permanently as instantaneous parameters in the memory while the parameter values of the control parameters of the second category are stored first for only a limited predetermined period of time.

In addition, it may be advantageous for all cases of programming instructions containing control parameters of the second category if the personal medical device offers the possibility of implementing a certain operating mode after receipt of such a programming instruction. In the case of a personal medical device in the form of a cardiac pacemaker, cardioverter or defibrillator, this may be an essentially known VVI mode, AAI mode or DDD mode, etc.

The operating state (operating mode) is selected in each case so that it allows secure and safe operation of the personal medical device with the corresponding parameter values, in particular so that it is safe for the patient.

In addition, it is advantageous if the programmable controller is designed to send a data packet with physiological or operational data obtained during the predetermined period of time via the first or second data communication interface. Such a data packet may then be received by a service center, for example. The data packet may, for example, contain data representing an intracardiac electrocardiogram, which was recorded during the predetermined period of time—i.e., during the temporary reprogramming of the personal medical device—and which can then be analyzed by a physician remotely.

It can also be advantageous if the programmable controller is designed to receive and execute a programming instruction after the predetermined period of time has elapsed, with the programming instruction containing a control command that triggers permanent storage of the parameter values in the memory even for the parameter values of the second category. Thus, a physician who has analyzed an intracardiac electrocardiogram received from the personal medical device, and who has found that the selected parameter values for the control parameters of the second category are suitable, can permanently activate these parameter values by use of the programming instruction containing the corresponding control command.

The personal medical device is preferably designed so that the values that determine the performance of the personal medical device after receipt of a programming instruction, in particular the length of the predetermined period of time for temporary reprogramming of the personal medical device and the categorical characterizations, are also externally programmable from outside of the personal medical device, namely concretely via the first data communication interface for programming from the immediate vicinity.

As an alternative, the predetermined period of time may also be part of a programming instruction which contains parameter values for control parameters of the second category. Then the duration of the respective activation of a parameter value of the second category may be determined by the same programming instruction that contains the corresponding parameter value to be tested.

As already mentioned, the personal medical device is preferably an active medical implant such as a cardiac pacemaker or defibrillator/cardioverter. In this case it is advantageous if the data communication interface for remote programming of the personal medical device allows wireless communication with a range of up to five meters, and is designed according to the Medical Implant Communications Service Standard (MICS).

In the case of a medical implant, a control parameter of the first category is preferably the sensitivity of a ventricular input amplifier, while a preferred control parameter of the second category is a VT zone limit, where VT denotes the heart rate above which the personal medical device initiates treatment of a ventricular tachycardia (VT).

The goals defined in the introduction may also be achieved by an arrangement for remote programming of a programmable personal medical device which has at least one service center for programming the personal medical device from a distance in addition to a personal medical device of the type described above. The service center has at least one data communication interface for at least indirect connection of the service center to the personal medical device. Furthermore, the service center has a memory and a programming unit. The programming unit is designed so that in combination with the memory, it can generate a user interface for remote programming of the personal medical device, said interface being designed to allow a programming instruction to be compiled for the personal medical device. To do so, the remotely programmable controller parameters are preferably represented on the user interface in addition to which of the two categories they belong to. This user interface is accessible, for example, via a computer connected to the service center or via a programming device of the traditional type connected to the service center.

The service center is preferably designed so that it can receive data packets containing physiological data and/or operational data sent by the personal medical device. In this context, the programming device is preferably designed so that it stores this data in the memory of the service center.

In addition, in a preferred version of the invention, the programming unit of the service center is designed to generate a user interface on which the physiological data or operational data stored in the memory of the service center is displayed.

To finally confirm a programming instruction, which is initially issued only temporarily, with parameter values for control parameters of the second category such that the personal medical device is permanently programmed with these parameter values, the programming unit is especially preferably designed to generate a user interface which allows such a programming instruction to be confirmed by a user task. This programming unit is designed to generate a suitable programming instruction and then send it to the personal medical device. In this way, the service center can allows programming instructions to be easily compiled, temporary programming instructions can be checked on the basis of the data received by the personal medical device, and a temporary programming instruction may be confirmed (or not) so that it becomes permanent.

The invention also includes a method for remote programming of a personal medical device of the type described previously using an arrangement as described previously. This method comprises at least the steps of sending a programming instruction from the service center to the personal medical device and then as an additional method step, either permanent reprogramming of the personal medical device when the programming instruction contains only parameter values for control parameters of the first category, or temporary reprogramming of the personal medical device for a predetermined period of time when the programming instruction contains parameter values for control parameters of the second category as well as the subsequent return to the starting values of the parameter values temporarily reprogrammed in the meantime.

The method preferably comprises the additional method steps of (1) detecting physiological data and/or operational data during a predetermined period of time, and (2) sending a data packet containing the physiological data and/or operational data to the service center.

In addition, the method may also include the additional step of confirming the parameter values of the control parameters of the second category and therefore permanent reprogramming of the personal medical device using the parameter values of the second category.

Additional advantageous embodiments of the invention are derived from the combinations of features mentioned previously with one another in combinations that were not previously mentioned explicitly or with other features, which are derived from the following descriptions of an exemplary embodiment.

BRIEF DESCRIPTION OF THE DRAWINGS

The invention will now be explained in greater detail on the basis of an exemplary embodiment with reference to the figures. In the figures.

DETAILED DESCRIPTION OF PREFERRED VERSIONS OF THE INVENTION

Figure 1:
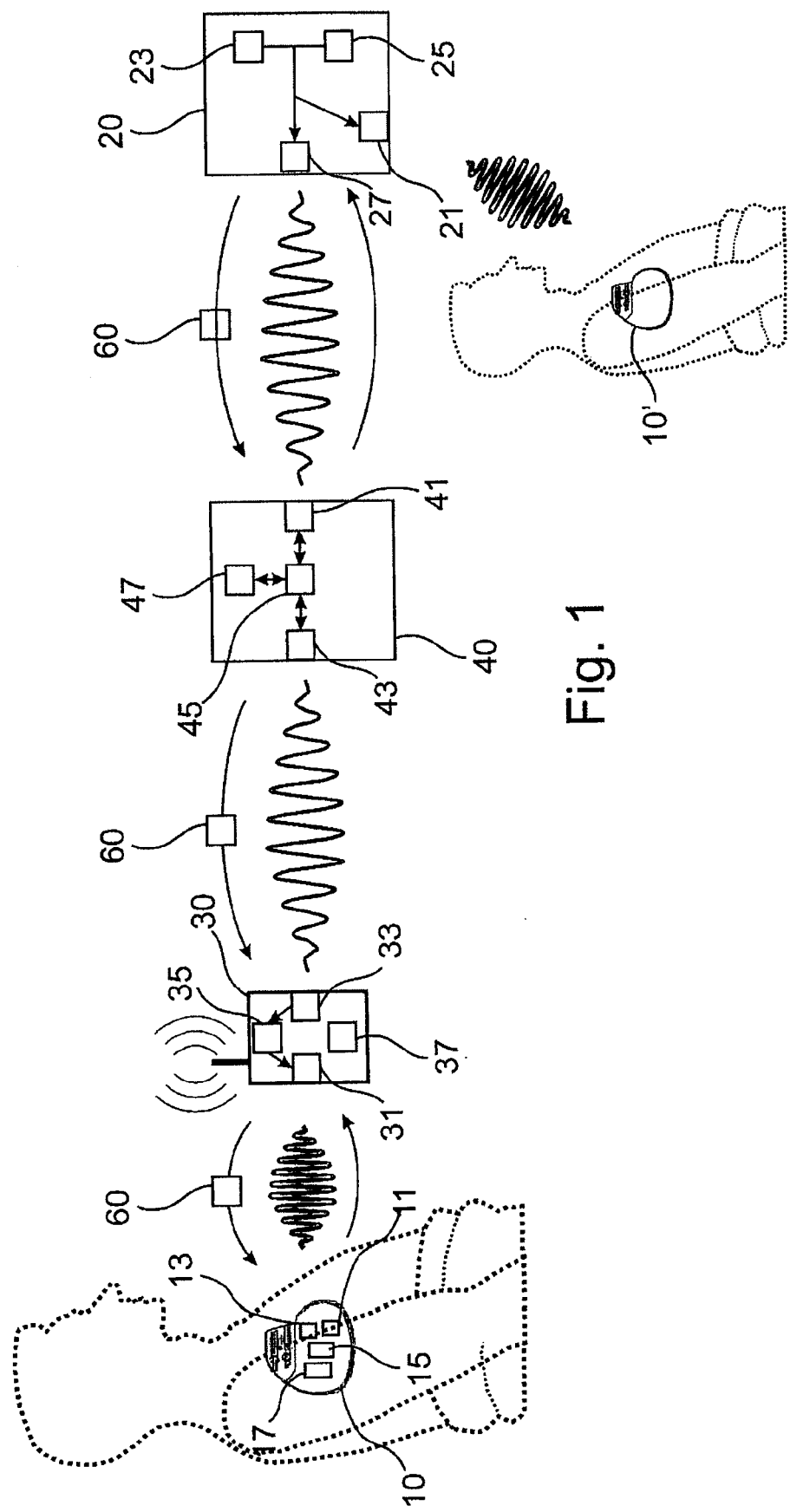
FIG. 1: shows an arrangement for remote programming of a personal programmable device.

The arrangement shown in FIG. 1 for remote programming of a personal medical device 10 comprises a patient intermediary device 30, a service center 40 and a programming device 20, in addition to the personal medical device 10 in the form of a cardiac pacemaker.

With the programming device 20, the implant 10 can be programmed directly via a very short-range wireless data link. Then with the help of the patient intermediary device 30 and the service center 40, the implant 10 can also be programmed remotely. In this case, the patient intermediary device 20 may also be connected to the service center 40 to thereby display a user interface generated with the help of the service center 40 for remote programming of the implant 10.

To be able to exchange data bidirectionally with the programming device 20 as well as with the service center 40 from a distance, the patient intermediary device has two data communication interfaces 11 and 13. The first data communication interface 11 allows short-range data communication directly with the programming device 20. The second data communication interface 13 of the implant 10 serves to establish a wireless data link between the implant 10 and the patient intermediary device 30. This data link is not of a particularly great range. The patient intermediary device will usually always be near the implant 10 and then serves as a station for further data transmission to and from the service center 40.

Both data communication interfaces 11 and 13 are connected to a programmable controller 15 of the implant, which is in turn connected to a memory 17.

The patient intermediary device 30 also has a first data communication interface 31 for wireless data exchange with the implant 10 via its second data communication interface 13. Furthermore, the patient intermediary device 30 also has a second data communication interface 33, which is designed to establish a data link to the service center 40. The first and second data communication interfaces 31 and 33 of the patient intermediary device 30 are interconnected at least indirectly via a control unit 35 of the patient intermediary device 30. In addition, the patient intermediary device 30 has its own memory 37 in which data, e.g., programming instructions 60, can be stored temporarily if they have been received by the service center 40, for example, but have not yet been transferred further to the implant 10.

The service center 40 also has a first data communication interface 43 which serves the function of data communication with the patient 30. The data link between the second data communication interface 33 of the patient intermediary device 30 and the first data communication interface 43 of the service center 40 may be accomplished via a hardwired connection, e.g., using a landline telephone network.

The service center 40 also has a control unit 45 and a memory 47 connected to it. The control unit 45 and the memory 47 in combination with one another also constitute a programming unit for remote programming of the implant 10. In particular the control unit 45 and the memory 47 of the service center 40 are designed so that they are able to generate a user interface for remote programming of the implant 10, which allows a user to compile a programming instruction for the implant. In this regard, the service center 40 may be connected via the Internet, for example, to a physician's computer on whose display screen the user interface for remote programming of the implant is then displayed.

Figure 2:
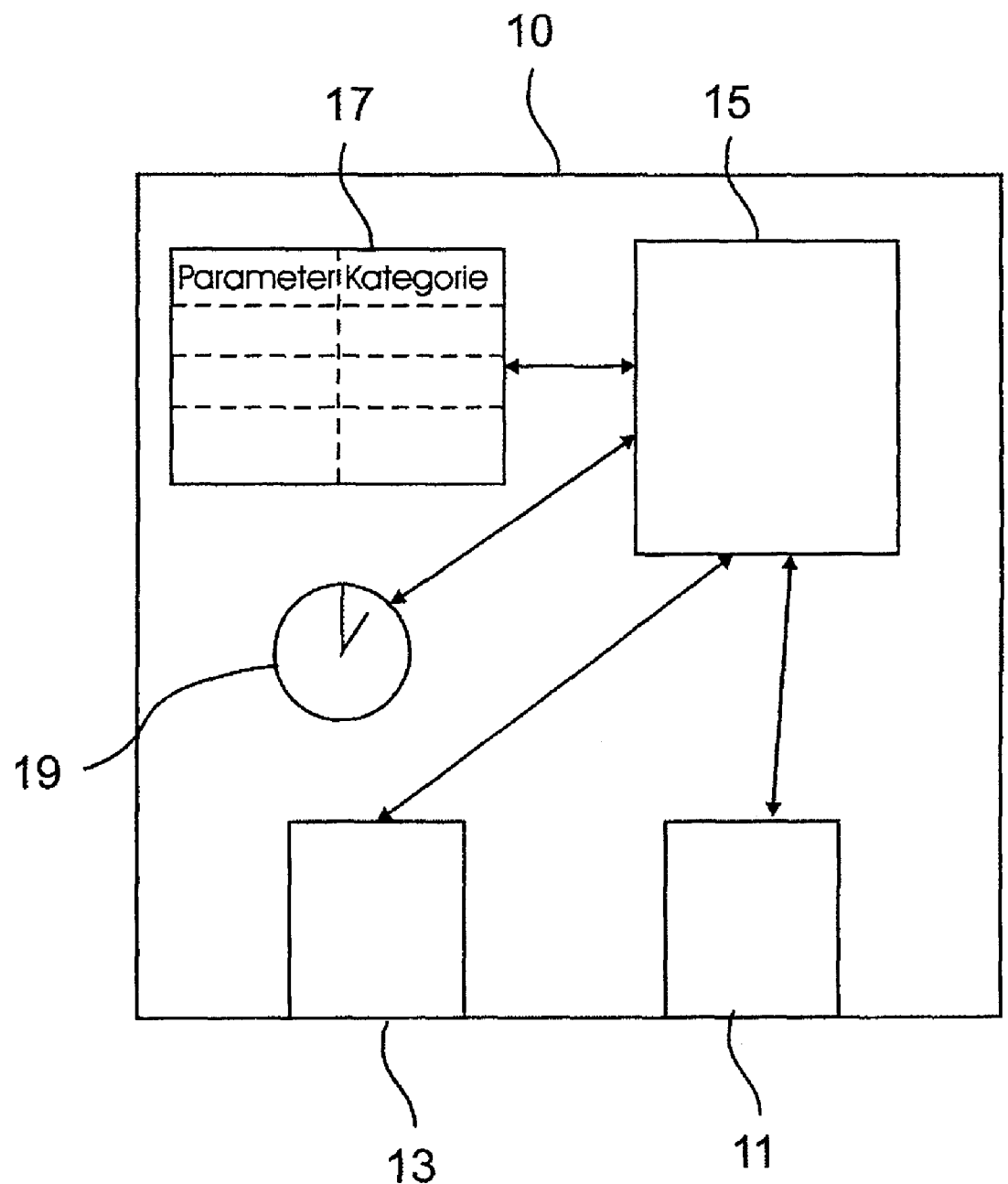
FIG. 2: shows the personal programmable device in a detailed view.

As shown in FIG. 2 in particular, the memory of the implant 17 is organized in combination with the controller 15 in such a way that in addition to currently storing the values required for control of the implant it also stores categorical characterizations assigned to these control parameters. The parameter values of the control parameters stored in the memory 17 then determine the functioning of the controller 15 and thus of the implant 10. The categorical characterizations determine the behavior of the implant in remote programming in which the implant 10 receives a programming instruction 60 via the second data communication interface 13.

The categorical characterizations stored in the memory 17 may then be altered only in the case of a direct data link between the implant 10' and the programming device 20, as illustrated at the lower right of FIG. 1. The categorical characterizations cannot be changed by way of remote programming.

For the remote programming, the implant 10 also has a timer 19, which is connected to the programmable controller 15 and allows it to alter control parameter values for a period of time which is predetermined by the timer in the sense of a received programming instructions, and to return to the parameter values prevailing originally after the predetermined period of time has elapsed.

The performance of the implant 10, which is determined by the corresponding design of the programmable controller 15 in combination with the memory 17, will now be explained in greater detail.

If the implant 10 receives via the second data communication interface 13 a programming instruction 60 containing only those parameter values belonging to controlled parameters of a first category, which is designated below as class 1, then these parameter values are immediately stored permanently in the corresponding location in the memory 17 so that they henceforth determine the functioning of the implant 10. Whether a respective parameter value is among the control parameters of the first or second category is determined for the implant 10 from the corresponding categorical characterization, which is stored for each respective control parameter in the memory 17. Remote programming of the implant 10 with parameter values for control parameters of class 1 therefore does not require an acknowledgement to the programming physician.

If a programming instruction contains parameter values of such control parameters that are classified in a second category which is designated as class 2, then at least these parameter values are activated only for a limited predetermined period of time, which is determined by the timer 19, in the sense that they are stored as the parameter values, which determine the function of the implant for the duration of the predetermined period of time.

Figure 3:
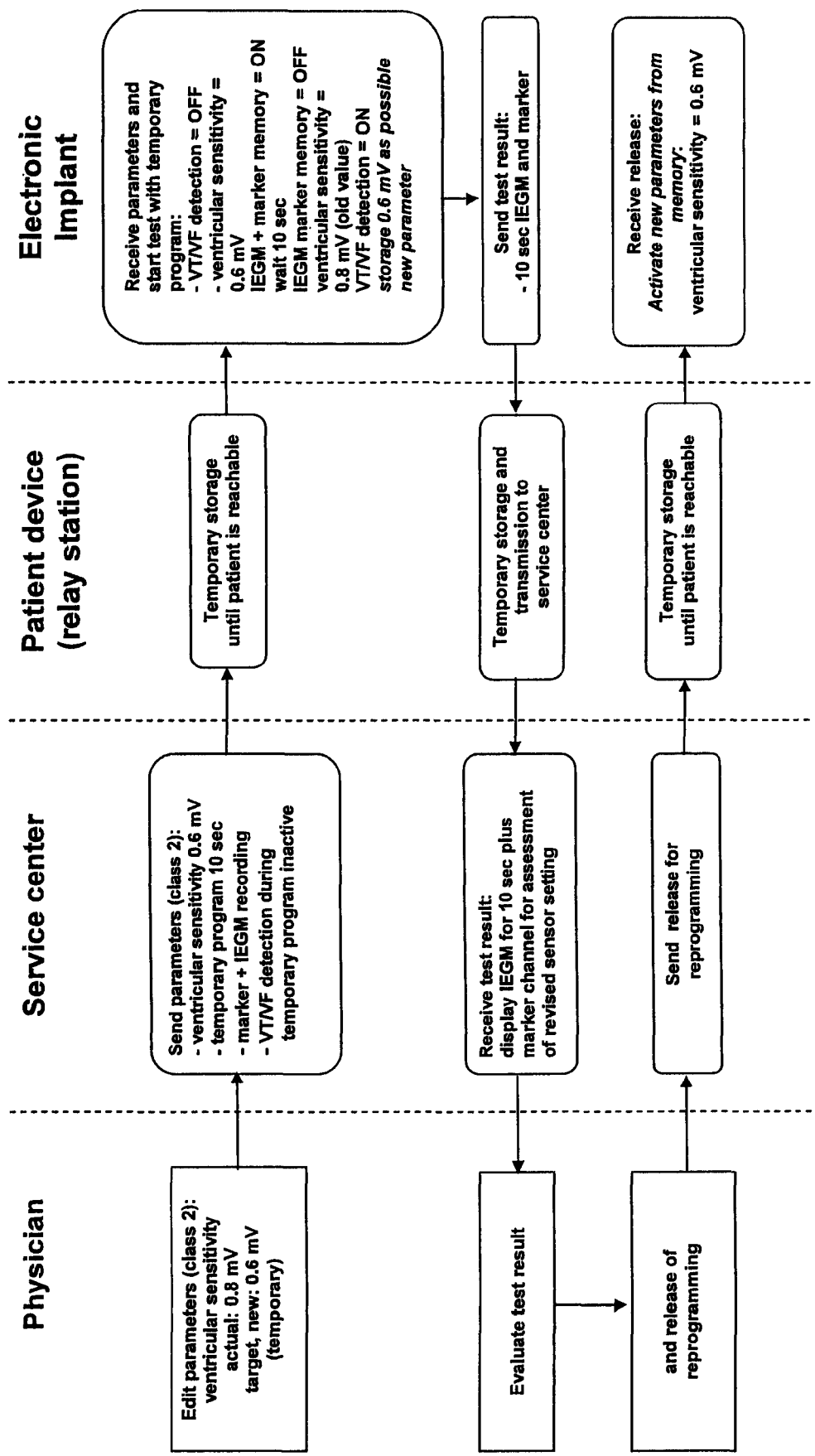
FIG. 3: shows the sequence of remote programming of the personal medical device with an arrangement according to FIG. 1 in a first variant.
Figure 4:
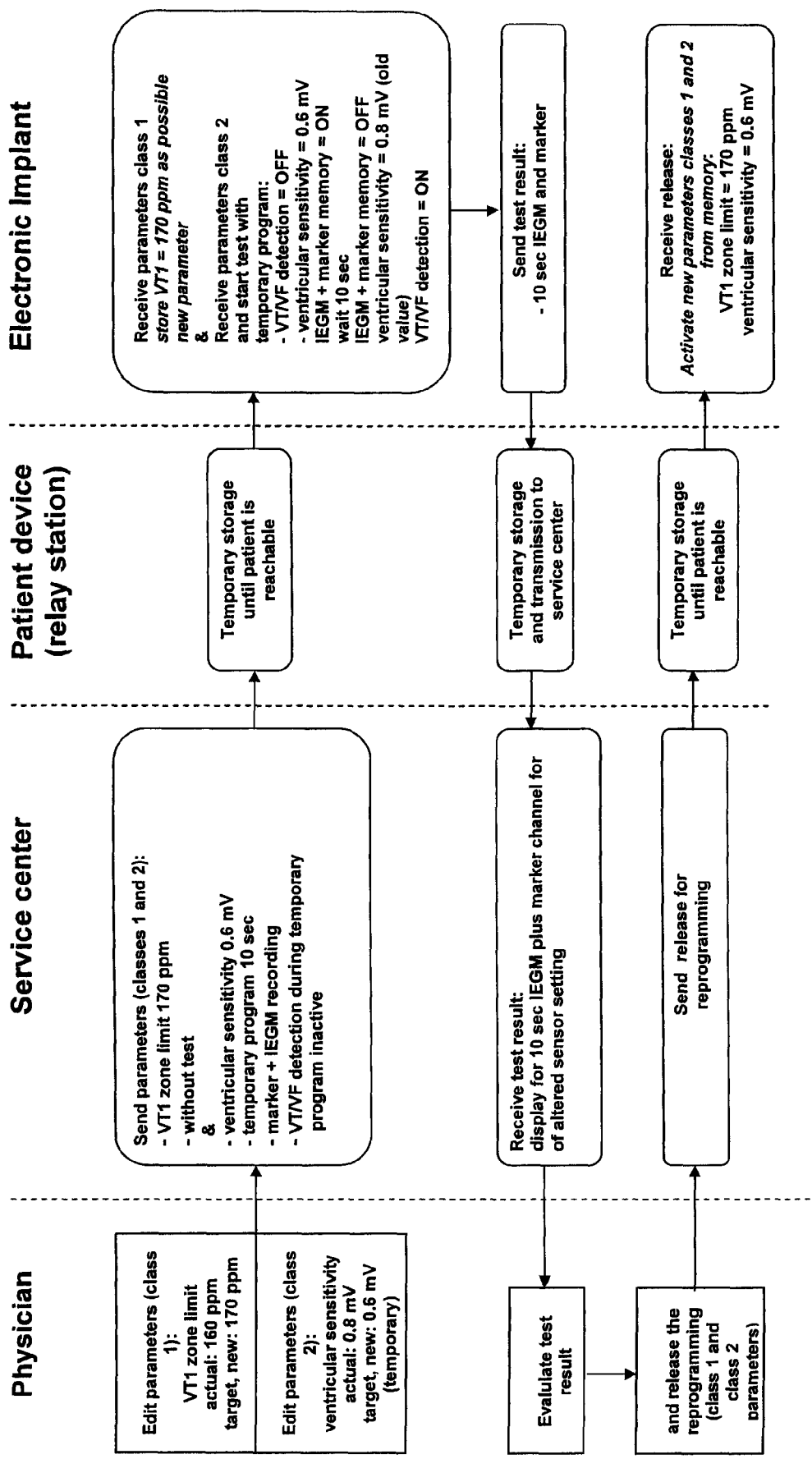
FIG. 4: shows the sequence of remote programming with a personal medical device with an arrangement according to FIG. 1 in a second variant.
Figure 5:
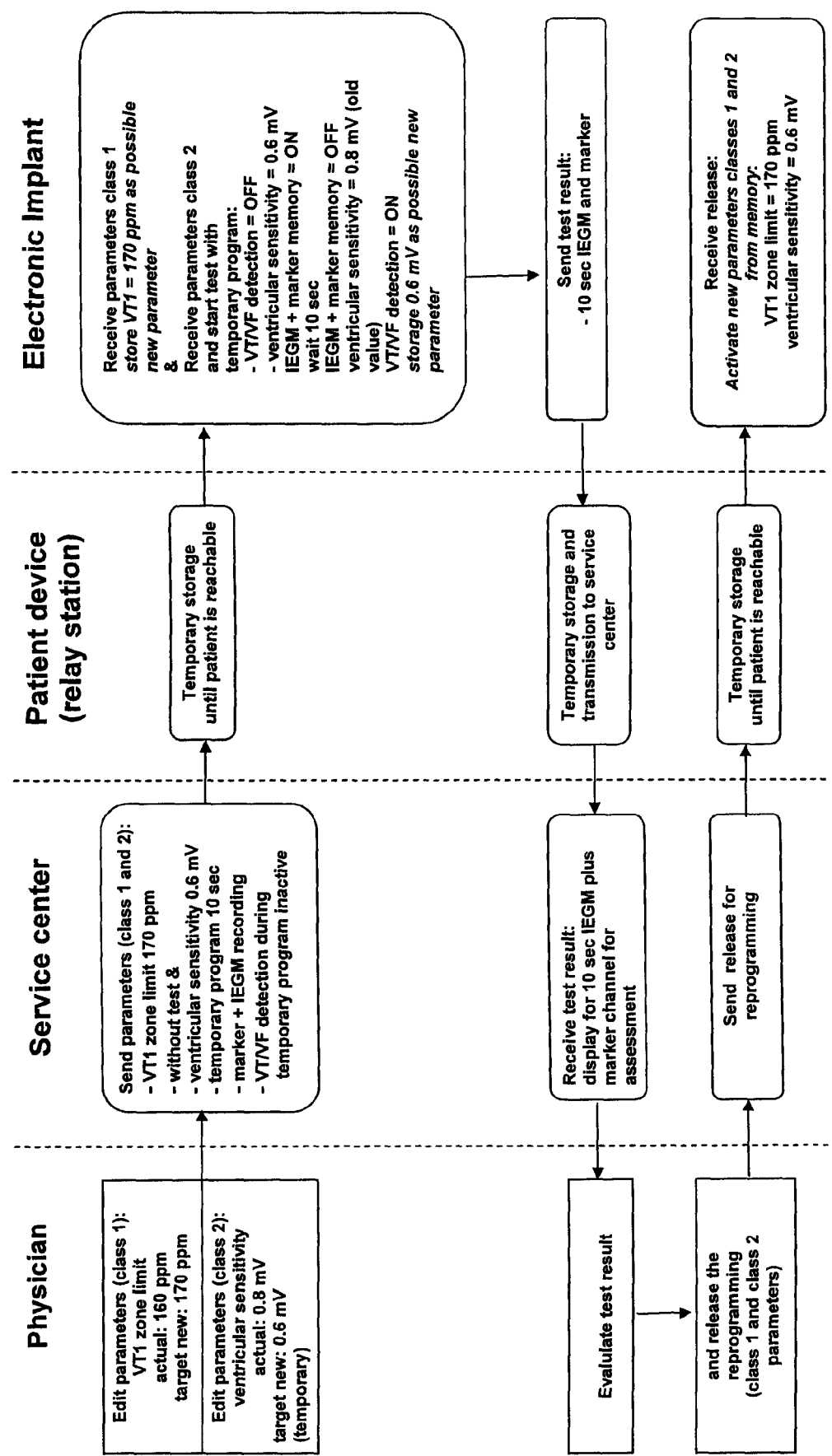
FIG. 5: shows the sequence of remote programming of the personal medical device with an arrangement according to FIG. 1 in a third variant.

Specific examples are illustrated in FIGS. 3 through 5.

FIG. 3 shows an example in which a programming instruction contains only parameters for control parameters of the second category (class 2). Specifically this is a parameter value for the control parameter "ventricular sensitivity" which defines the sensitivity of a ventricular input amplifier of a cardiac pacemaker. The sensitivity (response threshold) before programming is 0.8 mV. The programming instruction should increase the sensitivity so the response threshold is 0.6 mV.

Via a user interface generated by the service center, the physician enters the desired ventricular sensitivity and the service center generates from this data a programming instruction containing the new value for the ventricular sensitivity and also the duration of the predetermined period of time, namely 10 seconds. In addition, the programming instruction contains control commands which order the implant to record an intracardiac electrocardiogram (IEGM) for 10 seconds and marker signals. With a time reference to the intracardiac electrocardiogram, a marker signal indicates, for example, when a ventricular contraction has been detected, i.e., when the signal applied at the input of the ventricular input amplifier exceeded the response threshold of 0.6 mV. The increased sensitivity of the ventricular input amplifier may result in the ventricular detection channel responding not only to original ventricular events, i.e., ventricular contractions represented by an R wave in the intracardiac electrocardiogram but instead responds also to T waves, for example. It may then happen that the increased ventricular sensitivity results in the implant determining a presumed heart rate that is detected as ventricular tachycardia (VT) or as ventricular fibrillation (VF). To prevent this, detection of such tachycardias is deactivated by the programming instruction.

The service center then sends the corresponding programming instruction to the implant via the patient intermediary device.

The parameter values and the control commands received with the programming instruction are activated there for the predetermined period of time (10 seconds). Then the implant detects ventricular events with a response threshold of 0.6 mV and at the same time generates an intracardiac electrocardiogram (IEGM) with marker signals which indicate when the response threshold of 0.6 mV has been exceeded. After 10 seconds, the implant sends the intracardiac electrocardiogram (IEGM) thus detected and the marker signals in the form of a data packet to the service center via the patient intermediary device. At the same time, the implant returns to the parameter values and control commands in effect before the temporary reprogramming.

The service center with its control unit and memory is designed so that it generates a user interface from the data packet received by the implant, the received intracardiac electrocardiogram and the marker signals for the position being displayed on this interface. After observing this data, the physician may decide whether to make the reduction in the response threshold for the ventricular sensitivity permanent or whether it should remain so that the implant continues to operate on the basis of the original parameters.

If the physician decides to make the changes in the response threshold permanent, he can notify the service center of this through a voice operating element on the user interface. Then the service center generates a programming instruction with a control command for release of the reprogramming. This programming instruction is transmitted to the implant via the patient intermediary device.

The implant is designed so that it performs the permanent reprogramming of the parameter value for the ventricular sensitivity on the basis of such a programming command. Only this parameter value is altered. The setting with regard to detection of ventricular tachycardias or ventricular fibrillations as well as with regard to the recording of an intracardiac electrocardiogram (IEGM) remains at their original level, i.e., detection of ventricular tachycardias or fibrillations is activated and the recording of intracardiac electrocardiograms is deactivated after 10 seconds. This concludes reprogramming in the exemplary embodiment according to FIG. 3.

FIG. 4 shows an exemplary embodiment in which, in addition to the reprogramming of the ventricular sensitivity as described above, a zone limit for detecting a ventricular tachycardia of the first order is also to be altered. This should be increased from 160 beats per minute to 170 beats per minute. The VT1 zone limit here is a parameter of the first category (class 1) which is fundamentally reprogrammable without requiring an acknowledgement to the physician, so the reprogramming could be made permanently effective immediately.

After input of the corresponding values via the user interface, the service center generates a corresponding programming instruction and sends it to the electronic implant via the patient intermediary device. The reprogramming of the ventricular sensitivity is performed in this implant. This parameter value is activated for 10 seconds and then is reset at the original sensitivity level.

As in the preceding example, the implant generates an intracardiac electrocardiogram for 10 seconds as well as generating marker signals and then sends a corresponding data packet to the service center. The service center orders automatic display of this data on a user interface, which allows the physician to assess the data. The physician may then order the that a programming instruction be generated by a corresponding input via the user interface, this programming instruction causing both stored changes in the parameter values, namely for the ventricular sensitivity on the one hand and for the VT1 zone limit on the other hand, to become permanently effective.

After receiving this programming instruction, the implant sets these parameter values as the parameter values to henceforth be in effect permanently.

This concludes the reprogramming according to the exemplary embodiment in FIG. 4.

Finally, FIG. 5 shows an exemplary embodiment which is very similar to that in FIG. 4.

The difference is that the reprogramming of the control parameter of category 1 (in this case, the VT1 zone limit) becomes effective immediately and does not just become effective after confirmation of the revised sensitivity by the physician.

Accordingly, the physician must also confirm only the reprogramming of the ventricular sensitivity. A corresponding programming instruction to be generated by the service center therefore contains a control command that causes permanent reprogramming of the ventricular sensitivity. Permanent reprogramming of the VT zone limit has already been accomplished by the first programming instruction sent previously.

What is claimed is:

1. A programmable personal device (10), in particular an implantable medical device such as a cardiac pacemaker, cardioverter, defibrillator or the like, including:
   a. a first data communication interface (11) for a wireless data transmission, wherein the personal device is able to receive data containing programming instructions via the first data communication interface,
   b. a second data communication interface (13) for a wireless data transmission, wherein the personal device is also able to receive data containing programming instructions via the second data communication interface (13), and wherein the second data communication interface (13) differs from the first data communication interface (11) with regard to one or more of:
      (1) the data format required for the data transfer, and
      (2) the data transfer technique for the data transfer,
   c. a memory (17),
   d. a programmable controller (15) connected to the memory (17), wherein the programmable controller (15):
      (1) is at least indirectly connected to the first and second data communication interfaces (11, 13)
      (2) controls functions of the personal device on the basis of control parameters,
      (3) stores, in combination with the memory (17):
         (a) at least one instantaneous control parameter value, and
         (b) one categorical characterization for each control parameter, wherein the categorical characterization indicates:
            i. that a particular control parameter belongs to one of at least a first category and a second category, and
            ii. how the programmable controller (15) performs after receipt of a programming instruction via the second data communication interface (13),
      (4) has functionality defined such that after execution of a programming instruction which contains only control parameter values for control parameters of:
         (a) a first category, these control parameters are stored permanently as instantaneous control parameter values in the memory (17), so that the function of the programmable controller is determined by these control parameter values until receipt of another programming instruction;
         (b) a second category, these control parameter values are stored for a predetermined limited period of time as instantaneous control parameter values in the memory (17), so that the function of the programmable controller (15) is determined by these control parameters until the end of the predetermined period of time and then again by the control parameter values set previously.

2. The programmable personal device of claim 1 wherein the programmable controller stores all the control parameter values for a predetermined limited period of time as instantaneous control parameter values in the memory after execution of a programming instruction containing control parameter values for control parameters of both a first and a second category, whereby the function of the programmable controller is determined by these control parameter values until the end of the predetermined period of time and then is determined again by the control parameter values set previously.

3. The programmable personal device of claim 1 wherein the programmable controller, after execution of a programming instruction which contains control parameter values for control parameters of both a first and a second category, stores:
   a. the control parameter values of the control parameters of the first category permanently as instantaneous control parameter values in the memory, so that the function of the programmable controller is determined by these control parameter values until the end of another programming instruction, and
   b. stores the control parameter values of the control parameters of the second category for a predetermined limited period of time as instantaneous control parameter values in the memory, so that the function of the programmable controller is determined by these control parameter values until the end of the predetermined period of time, and the control parameters of the second category are then again determined by the control parameter values set previously.

4. The programmable personal device of claim 1 wherein the programmable controller places the personal device in a predetermined operating state for a predetermined period of time after execution of a programming instruction containing the control parameter values for control parameters of the second category.

5. The programmable personal device of claim 1 wherein the programmable controller sends a data packet containing the physiological or operational data obtained during the predetermined period of time over the first or second data communication interface after the predetermined period of time has elapsed.

6. The programmable personal device of claim 1 wherein the programmable controller receives and executes a programming instruction after a predetermined period of time has elapsed, the programming instruction containing a control command that triggers permanent storage of the control parameter values for control parameters of the second category in the memory.

7. The programmable personal device of claim 1 wherein the programmable controller:
   a. receives via a first data communication interface programming instructions which contain:
      (1) a value for the predetermined period of time, and/or
      (2) categorical characterizations for the control parameters, and
   b. stores this value and/or these categorical characterizations in the memory as a value to be applied henceforth and/or as categorical characterizations to be applied henceforth.

8. The programmable personal device of claim 1 wherein the personal device is an active medical implant.

9. The programmable personal device of claim 1 wherein the personal device is an implantable cardiac pacemaker or defibrillator/cardioverter.

10. The programmable personal device of claim 1 wherein the second data communication interface of the personal device provides wireless communication with a range of up to approximately five meters.

11. The programmable personal device of claim 1 wherein the control parameters include:
   a. a ventricular sensitivity of a ventricular input amplifier, the ventricular sensitivity being characterized as a control parameter of the first category, and
   b. a VT zone limit, the VT zone limit being characterized as a control parameter of the second category.

12. The programmable personal device of claim 1 in combination with a service center (40) for programming the personal device from a distance, wherein the service center includes:
   a. a data communications interface (43) for at least indirect connection of the service center to the personal device,
   b. a memory (47), and
   c. a programming unit (45) for the personal device, the programming unit (45) generating a user interface for remote programming of the personal device (10) so that the control parameters that are programmable for the personal device and possible control parameter values are displayed on the user interface for compiling a programming instruction for the programmable personal device.

13. The combination of claim 12 wherein:
   a. the service center receives data packets containing physiological and/or operational data transmitted by the personal device, and
   b. the programming unit stores this data in the memory of the service center.

14. The combination of claim 13 wherein the programming unit generates a user interface on which the physiological and/or operational data stored in the memory of the service center is displayed.

15. The combination of claim 14 wherein the programming unit generates a user interface allowing:
   a. confirmation of a programming instruction containing control parameter values for control parameters of the second category by a user input after the predetermined period of time has elapsed, and then
   b. generation of a corresponding programming instruction which is sent to the personal device.

16. The combination of claim 12 wherein:
   a. a programming instruction is sent from the service center to the personal device,
   b. the personal device is either:
      (1) permanently reprogrammed when the programming instruction contains only control parameter values for control parameters of a first category,
      (2) temporarily reprogrammed for a predetermined period of time when the programming instruction contains control parameter values for control parameters of a second category, with the control parameter values reverting to their original values thereafter.

17. The combination of claim 16 wherein:
   a. physiological data and/or operational data is detected during the predetermined period of time, and
   b. a data packet containing the physiological data and/or operational data is thereafter sent to the service center.

18. The combination of claim 17 wherein:
   a. the control parameter values of the control parameters of the second category are confirmed, and
   b. the personal device is thereafter reprogrammed with the control parameter values of the second category.

19. A method for programming a programmable personal device (10), in particular an implantable medical device such as a cardiac pacemaker, cardioverter, defibrillator or the like, wherein the personal device includes:
   A. a first data communication interface (11) for a wireless data transmission, wherein the personal device is able to receive data containing programming instructions via the first data communication interface,
   B. a second data communication interface (13) for a wireless data transmission, wherein the personal device is also able to receive data containing programming instructions via the second data communication interface (13), and wherein the second data communication interface (13) differs from the first data communication interface (11) with regard to one or more of:
      i. the data format required for the data reception, and
      ii. the data transfer technique for the data reception,
   C. a memory (17),
   D. a programmable controller (15) connected to the memory (17), wherein the programmable controller (15):
      i. is in communication with the first and second data communication interfaces (11, 13),
      ii. controls functions of the personal device on the basis of control parameters,
      iii. stores, in combination with the memory (17):

(1) at least one control parameter value, and
(2) a categorical characterization for each control parameter, wherein the categorical characterization indicates that a particular control parameter belongs to one of at least a first category and a second category, the method including the steps of:
a. sending a programming instruction from a service center to the personal device,
b. if the programming instruction contains only control parameter values for control parameters of the first category, storing these control parameter values in the memory (17) and defining the function of the programmable controller in accordance with these control parameter values at least until receipt of another programming instruction;
c. if the programming instruction contains only control parameter values for control parameters of the second category, storing these control parameter values in the memory (17) for a predetermined limited period of time and defining the function of the programmable controller in accordance with these control parameter values until the end of the predetermined period of time, and thereafter by any control parameter values previously stored in the memory (17).

20. A method for programming a programmable personal device wherein the personal device includes:
A. a first wireless data communication interface, wherein the personal device is able to wirelessly receive programming instructions via the first data communication interface,
B. a second wireless data communication interface, wherein the personal device is also able to wirelessly receive data programming instructions via the second data communication interface, and wherein the data format of the second wireless data communication interface differs from the data format of the first wireless data communication interface,
C. a memory storing the data programming instructions received from at least one of the first and second wireless data communication interfaces, at least some of the data programming instructions having control parameters of either:
  i. a first category indicating at least semi-permanent data programming instructions, and
  ii. a second category indicating temporary data programming instructions,
D. a programmable controller in communication with the memory, wherein the programmable controller controls functions of the personal device in accordance with the data programming instructions received from at least one of the first and second wireless data communication interfaces, the method including the steps of:
a. sending a programming instruction from a service center to the personal device,
b. if the programming instruction contains only the first category of control parameters,
  (1) storing the programming instruction in the memory, and
  (2) defining the function of the programmable controller in accordance with the programming instruction at least until receipt of another programming instruction;
c. if the programming instruction contains the second category of control parameters,
  (1) storing the programming instruction in the memory for a predetermined time period, and
  (2) defining the function of the programmable controller in accordance with the programming instruction until the end of the predetermined time period, and thereafter by any programming instruction previously stored in the memory.

* * * * *